United States Patent
Beyer et al.

(10) Patent No.: US 12,220,344 B2
(45) Date of Patent: Feb. 11, 2025

(54) INTERNAL CONDOM METHOD AND DEVICE

(71) Applicant: Craig F. Beyer, Boulder, CO (US)

(72) Inventors: Craig F. Beyer, Boulder, CO (US); Charles A. Patterson, Durango, CO (US)

(*) Notice: Subject to any disclaimer, the term of this patent is extended or adjusted under 35 U.S.C. 154(b) by 297 days.

(21) Appl. No.: 17/962,427

(22) Filed: Oct. 7, 2022

(65) Prior Publication Data

US 2023/0218428 A1    Jul. 13, 2023

Related U.S. Application Data

(60) Provisional application No. 63/297,780, filed on Jan. 9, 2022.

(51) Int. Cl.
*A61F 6/04* (2006.01)
*A61F 6/00* (2006.01)

(52) U.S. Cl.
CPC ............... *A61F 6/04* (2013.01); *A61F 6/005* (2013.01)

(58) Field of Classification Search
CPC .... A61F 6/04; A61F 6/005; A61F 6/18; A61F 6/08; A61F 6/14; A61F 6/20; A61F 6/06; A61F 6/144; A61F 2/0045; A61K 9/0036; A61M 31/002
See application file for complete search history.

(56) References Cited

U.S. PATENT DOCUMENTS

| | | | |
|---|---|---|---|
| 3,709,220 A | 1/1973 | Boyden | |
| 4,183,358 A * | 1/1980 | Cohen | A61F 6/02 |
| | | | 604/328 |
| 4,829,991 A * | 5/1989 | Boeck | A61F 5/41 |
| | | | 600/38 |
| 5,603,335 A | 2/1997 | McClenahan | |
| 2008/0078408 A1 | 4/2008 | Park | |

FOREIGN PATENT DOCUMENTS

| | | | |
|---|---|---|---|
| CN | 102302394 A | 11/2012 | |
| DE | 504554 A * | 8/1930 | ............... A61F 6/02 |
| DE | 504554 C | 8/1930 | |
| DE | 19704626 A1 | 8/1998 | |
| ES | 2012848 A * | 4/1990 | ............... A61F 5/42 |
| ES | 2012848 A6 | 4/1990 | |

(Continued)

OTHER PUBLICATIONS

International Search Report and Written Opinion issued Mar. 29, 2023 in related international patent application No. PCT/US22/46128, 13 pgs.

*Primary Examiner* — Ophelia A Hawthorne

(74) *Attorney, Agent, or Firm* — Fox Law Group, LLC; Bradley Fox

(57) ABSTRACT

An intraurethral contraceptive device includes an insertion tool and a urethral sleeve inside the insertion tool. The urethral sleeve includes a balloon on an outer surface and a distal proximal end of the urethral sleeve, having an air lumen that extends to a distal end of the urethral sleeve. There is an inside reservoir at a distal end of the sleeve, configured to capture any fluid traveling from the proximal end to the distal end of the urethral sleeve. An insertion plunger is coupled to a plunger head. The insertion plunger is configured to be placed inside a distal end of the insertion tool.

21 Claims, 8 Drawing Sheets

(56) References Cited

FOREIGN PATENT DOCUMENTS

| KR | 20110039680 | A |   | 5/2012 |   |
|----|------------|---|---|--------|---|
| MD | 4441 | C1 |   | 6/2017 |   |
| RU | 2372059 | C1 |   | 11/2009 |   |
| WO | 2003088879 | A1 |   | 10/2003 |   |
| WO | WO-03088879 | A1 | * | 10/2003 | ........... A61F 2/0009 |
| WO | 2006112632 | A1 |   | 10/2006 |   |

* cited by examiner

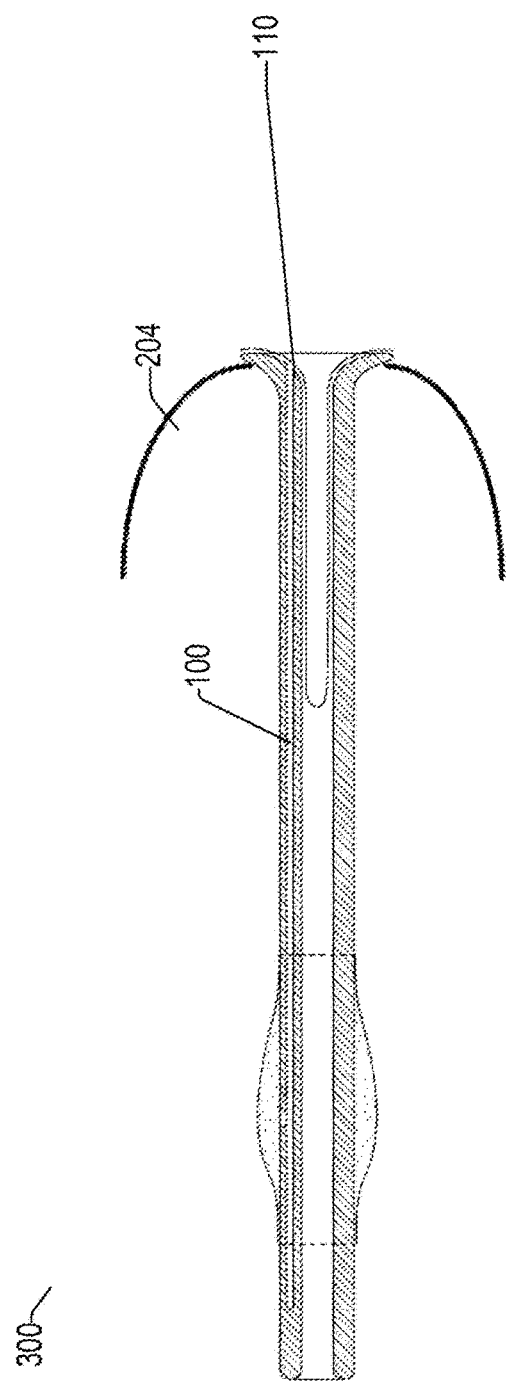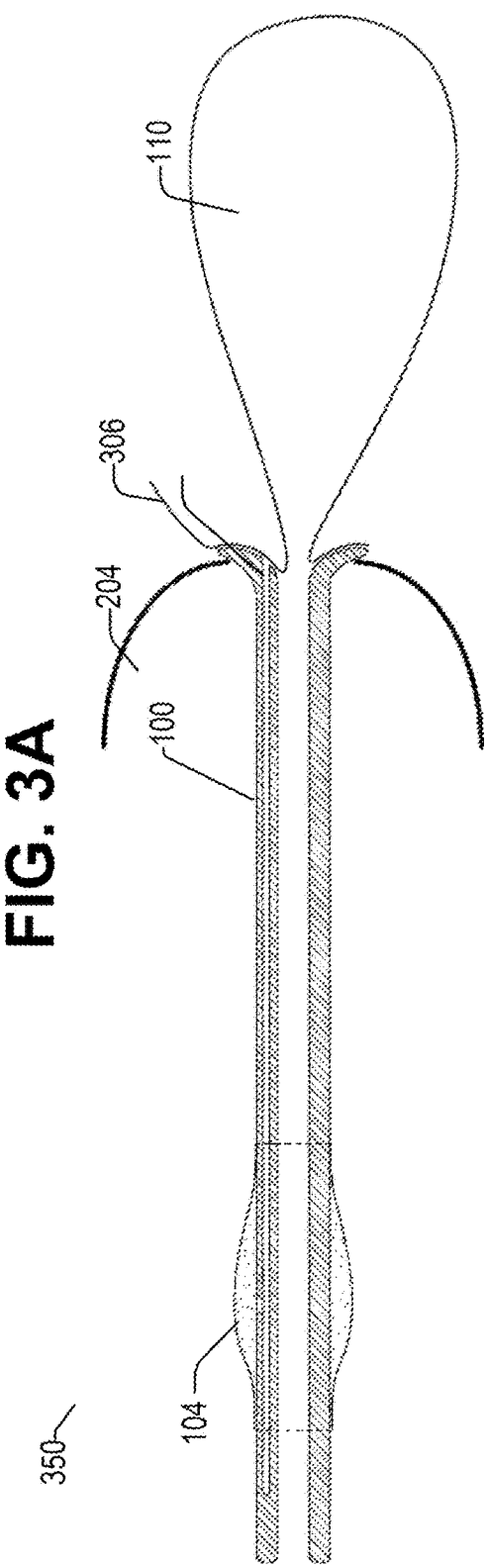
FIG. 3A
FIG. 3B

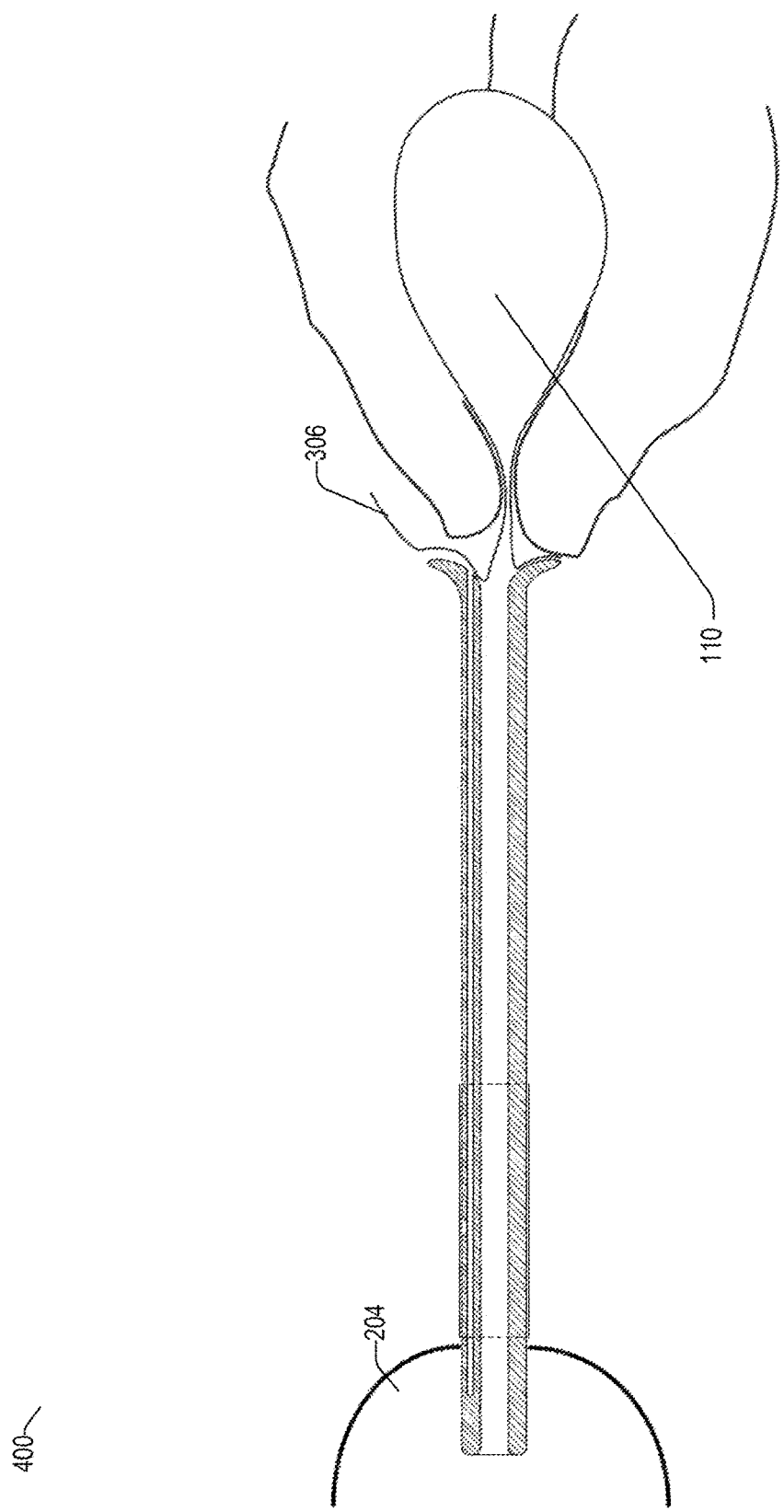

INTERNAL CONDOM METHOD AND DEVICE

CROSS REFERENCE TO RELATED APPLICATIONS

The present application claims the benefit of priority under 35 U.S.C. § 119 from U.S. Provisional Patent Application Ser. No. 63/297,780, entitled "Internal Condom Method and Device," filed on Jan. 9, 2022, which is hereby incorporated by reference in their entirety for all purposes.

BACKGROUND

Technical Field

The present disclosure generally relates to a male contraceptive device, and more particularly, to internal urethral condoms and methods of using the same.

Description of the Related Art

A condom is a physical barrier that conforms to the shape of a penis that acts as a barrier during sexual intercourse to reduce the probability of pregnancy and/or a sexually transmitted disease (STD). In additional to dramatically reducing the probability of pregnancy, it also can substantially reduce various diseases such as HIV/AIDS, Chlamydia, gonorrhea, hepatitis B, trichomoniasis, etc. Known condoms are generally in the shape of an external sheath around an erect penis, referred to herein as a traditional condom. Although generally effective in purpose, known condoms are often rejected because partners may not experience sufficient physical association during sexual intercourse due to the physical membrane in between. Further, traditional condoms may slip during a moment of loss of erection, thereby leading to the very dangers it is intended to avoid. While more modern solutions exist, they typically do not include an adequate combination of effectiveness against pregnancy, physical sensation between partners, protection against STDs, and spermicidal protection. It is within these considerations and others that this application has been written.

SUMMARY

According to one embodiment, an intraurethral contraceptive device includes an insertion tool and a urethral sleeve inside the insertion tool. The urethral sleeve includes a balloon on an outer surface and a distal proximal end of the urethral sleeve, having an air lumen that extends to a distal end of the urethral sleeve. There is an inside reservoir at a distal end of the sleeve, configured to capture any fluid traveling from the proximal end to the distal end of the urethral sleeve. An insertion plunger is coupled to a plunger head. The insertion plunger is configured to be placed inside a distal end of the insertion tool.

In one embodiment, insertion tool is constructed of a rigid polyurethane and is substantially cylindrically shaped.

In one embodiment, the insertion tool includes a circumferential protruding member on an outer surface of the insertion tool configured to stop an insertion of the insertion tool into a urethra beyond a predetermined distance.

In one embodiment, the insertion tool is configured to compress the balloon. The balloon may be pre-inflated.

In one embodiment, the proximal end of the urethral sleeve is more rigid than its distal end. A rigidity of the proximal end is sufficient to prevent the balloon from narrowing a diameter of an opening (e.g., tract) of the urethral sleeve below a predetermined threshold.

In one embodiment, the balloon is pre-inflated in the insertion tool.

In one embodiment, the air lumen is sealed at the distal end of the urethral sleeve. The seal of the air lumen may be by way of adhesion to an outer wall of the urethral sleeve.

In one embodiment, the air lumen is configured to inflate the balloon to a predetermined pressure and to deflate the balloon upon a trigger. The trigger to deflate the balloon through the air lumen may be by way of a pullable tab at a distal end of the urethral sleeve.

In one embodiment, the insertion plunger includes a spring configured to push the insertion plunger back to an original position after a deployment of the urethral sleeve in the urethra.

In one embodiment, the proximal end of the insertion plunger abuts the distal end of the urethral sleeve inside the insertion tool.

In one embodiment, the insertion plunger is configured to slidingly release a proximal portion of the urethral sleeve including the balloon from a proximal end of the insertion tool into the urethra by a predetermined distance.

In one embodiment, there is a vasodilator inside the insertion tool.

According to one embodiment, a method of administering an intraurethral contraceptive device having an insertion tool, a urethral sleeve inside the insertion tool, and an insertion plunger at a distal end of the insertion tool is provided. The method includes slidingly inserting the insertion tool into a urethra. A proximal portion of the urethral sleeve including a balloon is released from a proximal end of the insertion tool into the urethra. The insertion tool together with the insertion plunger is slidingly removed from the urethra. Any fluid traveling from the proximal end to the distal end of the urethral sleeve is caught by a reservoir coupled to a distal end of the urethral sleeve. The balloon is deflated and the urethral sleeve removed from the urethra.

In one embodiment, a predetermined distance that the insertion tool can be inserted into the urethra is controlled by a circumferential protruding member on an outer surface of the insertion tool.

In one embodiment, the balloon expands upon releasing the proximal portion of the urethral sleeve into the urethra.

In one embodiment, the balloon is pre-inflated in the insertion tool.

In one embodiment, releasing of the proximal portion of the urethral sleeve includes slidingly reducing a distance between a plunger head of the insertion plunger and the distal end of the insertion tool, by a predetermined distance.

In one embodiment, deflating the balloon comprises pulling a tab at a distal end of the urethral sleeve, operative to open a seal of an air lumen leading to the balloon.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

FIG. 3A provides a cross-section view of a urethral sleeve that is inside a urethra after the insertion tool is removed, consistent with an illustrative embodiment.

FIG. 3B is a cross section view of a urethral sleeve after the reservoir catching any fluids in the tract of the urethral sleeve, consistent with an illustrative embodiment.

FIG. 4 illustrates a urethral sleeve having a deflated balloon, consistent with an illustrative embodiment.

DETAILED DESCRIPTION

Overview

Figure 1:
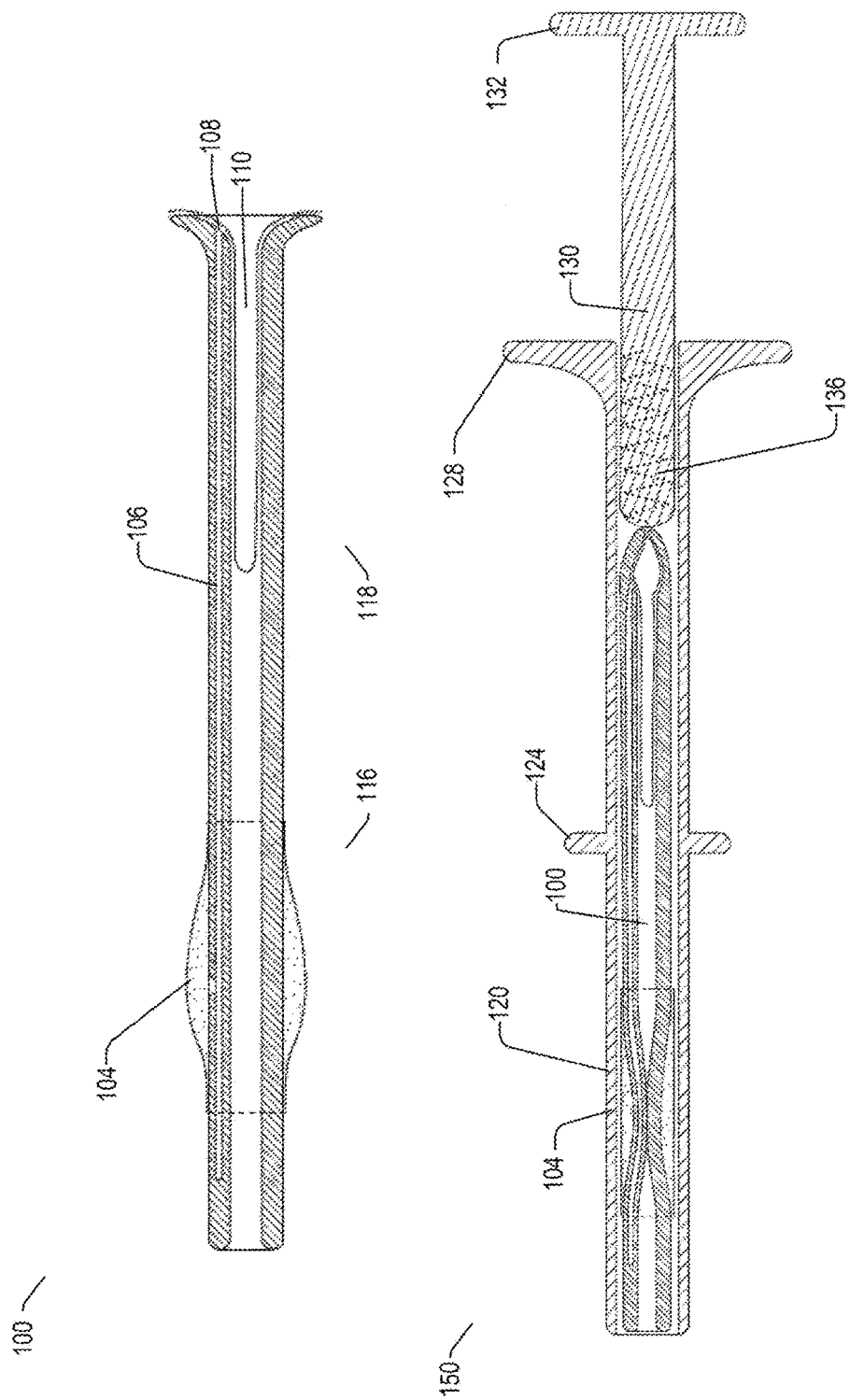
FIG. 1 illustrates an example male intraurethral contraceptive system (ICS), consistent with an illustrative embodiment.

In the following detailed description, numerous specific details are set forth by way of examples to provide a thorough understanding of the relevant teachings. However, it should be apparent that the present teachings may be practiced without such details. In other instances, well-known methods, procedures, components, and/or circuitry have been described at a relatively high-level, without detail, to avoid unnecessarily obscuring aspects of the present teachings. Various techniques are described in detail with reference to a few example embodiments thereof as illustrated in the accompanying drawings. In the following description, numerous specific details are set forth in order to provide a thorough understanding of one or more aspects and/or features described or reference herein. It will be apparent, however, to one skilled in the art, that one or more aspects and/or features described or reference herein may be practiced without some or all of these specific details. In other instances, well known process steps and/or structures have not been described in detail in order to not obscure some of the aspects and/or features described or reference herein.

One or more different concepts may be described in the present application. Further, for one or more of the concepts described herein, numerous embodiments may be described in this disclosure, and are presented for illustrative purposes only. The described embodiments are not intended to be limiting in any sense. One or more of the concepts may be widely applicable to numerous embodiments, as is readily apparent from the disclosure. These embodiments are described in sufficient detail to enable those skilled in the art to practice one or more of the present concepts, and it is to be understood that other embodiments may be utilized and that structural, logical, and other changes may be made without departing from the scope of the one or more of the concepts discussed herein. Accordingly, those skilled in the art will recognize that the one or more of the concepts may be practiced with various modifications and alterations. Particular features of one or more of the concepts may be described with reference to one or more particular embodiments or figures that form a part of the present disclosure, and in which are shown, by way of illustration, specific embodiments of one or more of the concepts. It should be understood, however, that such features are not limited to usage in the one or more particular embodiments or figures with reference to which they are described. The present disclosure is neither a literal description of all embodiments of one or more of the concepts nor a listing of features of one or more of the concepts that must be present in all embodiments.

Headings of sections provided in this disclosure and the title of this disclosure are for convenience only, and are not to be taken as limiting the disclosure in any way. A description of an embodiment with several components in communication with each other does not imply that all such components are required. To the contrary, a variety of optional components are described to illustrate the wide variety of possible embodiments of the present disclosure.

Further, although process steps, method steps, or the like may be described in a sequential order, such processes or methods may be configured to work in alternate orders. In other words, any sequence or order of steps that may be described in this application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary, and does not imply that the illustrated process is preferred.

When a single device or article is described, it will be understood that more than one device/article (whether or not they cooperate) may be used in place of a single device/article. Similarly, where more than one device or article is described (whether or not they cooperate), it will be readily apparent that a single device/article may be used in place of the more than one device or article.

The functionality and/or the features of a device may be alternatively embodied by one or more other devices that are not explicitly described as having such functionality/features. Thus, other embodiments need not include the device itself.

Techniques and mechanisms described or reference herein are sometimes described herein in singular form for clarity. However, it should be noted that particular embodiments include multiple iterations of a technique or multiple instantiations of a mechanism unless noted otherwise.

Although the terms first, second, etc., may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

Example embodiments are described herein with reference to cross-sectional illustrations and different views that are schematic illustrations of idealized or simplified embodiments (and intermediate structures). As such, variations from the shapes of the illustrations as a result, for example, of manufacturing techniques and/or tolerances, may be expected. Thus, the regions illustrated in the figures are schematic in nature and their shapes do not necessarily illustrate the actual shape of a region of a device and do not limit the scope. It should be appreciated that the figures and/or drawings accompanying this disclosure are exemplary, non-limiting, and not necessarily drawn to scale, unless a scale is specifically provided in that particular figure.

It is to be understood that other embodiments may be used and structural or logical changes may be made without departing from the spirit and scope defined by the claims. The description of the embodiments is not limiting. In particular, elements of the embodiments described hereinafter may be combined with elements of different embodiments.

Various aspects described or referenced herein are directed to different internal urethral condom devices (IUCDs) and methods of using thereof. The male contraceptive device includes an insertion tool. A urethral sleeve is inside the insertion tool, the urethral sleeve comprises a balloon on an outer surface and proximal end of the urethral sleeve. The balloon has an air lumen that extends to the distal end of the urethral sleeve. An inside reservoir at a distal end of the sleeve is configured to capture any fluid traveling from the proximal end to the distal end of the urethral sleeve. An insertion plunger is coupled to a plunger head, wherein the insertion plunger is configured to be placed inside the distal end of the insertion tool.

By virtue of the devices and methods discussed herein, in addition to preventing pregnancy, the spread of sexually transmitted diseases (STDs) can be substantially suppressed by preventing the escape of bodily fluids that may include, without limitation, human papilloma virus (HPV), Herpes simplex virus (HSV), Human immunodeficiency virus (HIV), Monkey pox, poliovirus, etc. These benefits are provided while maintaining full sensation between sexual partners.

The techniques described herein may be implemented in a number of ways. Example implementations are provided below with reference to the following figures.

Example Components of a Urethral Condom

FIG. 1 illustrates an example male intraurethral contraceptive system (ICS) 150, consistent with an illustrative embodiment. The ICS 150 includes a urethral sleeve 100, sometimes referred to herein as a catheter, having a first (e.g., proximal) end 116 and a second (e.g., distal) end 118 that are configured to prevent any fluids from being released from the second end 118. In various embodiments, the urethral sleeve 100 may comprise rubber, latex, silicone, TPE, and/or any other suitable material that provides sufficient flexibility and durability to be inserted and kept in a urethra for a prolonged period of time. In one embodiment, the urethral sleeve 100 also comprises a distal urethral stop configured to prevent the distal end of the urethral sleeve from passing beyond the fossa navicularis when inserted. For example, the cavernous portion of the urethra may be narrow, and of uniform size in the body of the penis (e.g., measuring about 6 mm in diameter and can stretch to 8 to 9 mm in diameter.) It is dilated anteriorly within the glans penis, where it forms the fossa navicularis urethrae which may be 10-11 mm diameter.

In one embodiment, the first end 116 is made more rigid than the second end 118. For example, the rigidity of the proximal end of the urethral sleeve 100 is sufficient to prevent the balloon from narrowing a diameter of an opening (e.g., tract) of the urethral sleeve below a predetermined threshold.

There is a balloon 104, sometimes referred to herein as a bladder, on an outer surface of the urethral sleeve 100. In one embodiment, the balloon 104 circumferentially covers the outer surface of at least a portion of the first end 116. The balloon 104 includes an air lumen 106 that extends from the first end 116 to the distal end of the urethral sleeve. In one embodiment, the balloon 104 is pre-inflated with a fluid, such as air, nitrogen, etc., through the air lumen 106 to a predetermined pressure. The air lumen 106 is sealed 108 at the distal end of the sleeve, for example, by way of adhesion to the outer wall (e.g., surface) at the distal end of the urethral sleeve. The air lumen 106 can later also be used to deflate the balloon 104, as will be discussed in more detail below.

There is an inside reservoir 110 configured to capture any fluid traveling from the proximal end to the distal end of the urethral sleeve 100. For example, the inside reservoir 110 may capture the fluid by turning inside-out and expanding sufficiently to capture this fluid at the distal end of the urethral sleeve 100.

By way of example only and not by way of limitation, the urethral sleeve 100 can have a length ranging from 3.5" to 6.5" and have a diameter at the first end 116 ranging from 2 mm to 6 mm (uninflated) to 10 mm when it is fully inflated. The second end 118 can remain constant in diameter ranging from 4 to 6 mm.

The urethral sleeve 100 is provided inside of an insertion tool 120 of the ICS 150. The insertion tool 120 can be cylindrically shaped, although other shapes, such as oval, are contemplated as well. The insertion tool 120 provides the structural integrity that is salient to be inserted into a urethra. The insertion tool 120 also provides the requisite compression of the pre-inflated balloon 104 of the urethral sleeve 100, such that the balloon 104 does not impede the sliding entry into a urethra. In various embodiments, the insertion tool 120 may comprise polyurethane or any other suitable material. In one embodiment, between the insertion tool and the urethral sleeve 100 there is a vasodilator, spermicidal, bactericidal, and/or virucidal lubricant.

The insertion tool 120 has a first (e.g., proximal) end and a second (e.g., distal) end, and configured to securely house the urethral sleeve 100 such that the balloon 104 is housed at the proximal end of the insertion tool 120. In one embodiment, the insertion tool 120 has a first protruding member 124, referred to herein as an insertion stop 124, at the distal end of the insertion tool 120. The insertion stop 124 can act as a physical barrier (i.e., stop) for the insertion of the insertion tool 120 into a urethra. In this regard, reference is made to FIG. 2, which provides cross section views 200 and 250 of an insertion tool 150 placed inside a urethra of a penis 204, consistent with an illustrative embodiment. Accordingly, the insertion tool 120 can be slidingly inserted into the urethra until the tip of the penis 204 abuts this insertion stop 124, thereby providing a physical barrier from further insertion into the urethra.

In one embodiment, the insertion tool 120 has a second protruding member 128, sometimes referred to herein as a plunger stop. The plunger stop 128 includes the function of a physical barrier from the insertion plunger 130 to be inserted more than a predetermined distance A.

The insertion plunger 130 is placed inside the insertion tool 120 from the distal end of the insertion tool 120. For example, after the insertion tool 120 is slidingly placed inside a urethra, the plunger head 132 can be pressed towards the plunger stop 128 of the insertion tool 120, such that the urethral sleeve is ejected inside a urethra (e.g., erect penis) by a predetermined distance A. The insertion plunger 130 has a first (e.g., proximal) end and a second (distal) end having a handle (i.e., plunger head 132). As shown in configuration 150 of FIG. 1, the proximal end of the insertion plunger 130 abuts the distal end of the urethral sleeve 100 inside the insertion tool 120.

Figure 2:
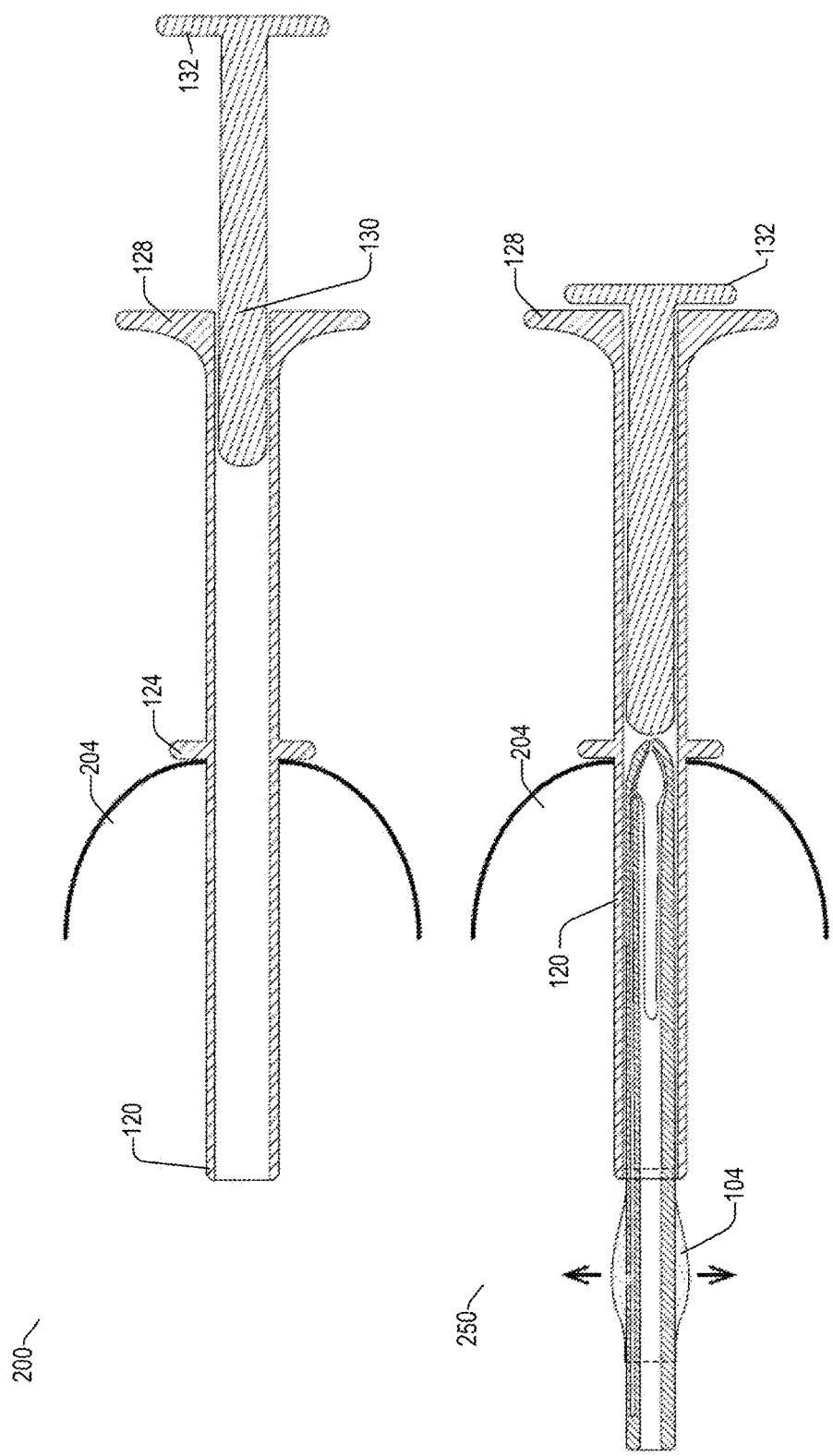
FIG. 2 provides cross-section views of an insertion tool placed inside a urethra, consistent with an illustrative embodiment.

As illustrated in cross section view 250 of FIG. 2, by pressing the plunger head 132 of the insertion plunger 130 towards the plunger stop 128, a portion of the urethral sleeve 100 is slidingly pushed outside the proximal end of the insertion tool 120 by a predetermined distance A such that the balloon can expand inside the urethra of the individual wearing the contraceptive device, thereby providing an occlusion between passage of any fluid from the urethral sleeve. Such expansion of the balloon also anchors the urethral sleeve within the urethra so that the urethral sleeve remains anchored internally as the insertion device is withdrawn and/or once it is completely removed. In one embodiment, instead of pushing the plunger head 132 towards the plunger stop 128, the plunger stop 128 can be pulled towards the plunger head 132 by the distance A. Referring back to FIG. 1, in one embodiment, the insertion plunger 130 has a spring 136, which pushes the insertion plunger 130 back to its original position after the deployment of the urethral sleeve 100 in the urethra.

Thus, the insertion plunger 130 allows the urethral sleeve 100 to be inserted into a (e.g., erect) penis. The insertion plunger 130 can then be slidingly removed from the urethra of the erect penis, together with the insertion tool 120, by pulling the handle of the plunger stop 128 away from the urethra. In this regard, FIG. 3A provides a cross-section view 300 of a urethral sleeve 100 that is inside a urethra after the insertion tool is removed, consistent with an illustrative embodiment. The balloon 104 anchors and prevents the urethral sleeve 100 from sliding out during the removal of the insertion tool 120 together with the insertion plunger 130, thereby leaving the urethral sleeve 100 securely inside the urethra. In one embodiment, a stop at the distal end of the urethral sleeve can be configured to stop at the head of the glans penis and/or within the fossa navicularis (e.g., the expanded portion of the distal end of the male urethra) within the glans penis so that the stop is completely internalized and not visible externally.

FIG. 3B is a cross section view 350 of a urethral sleeve 100 after the reservoir 110 catching any fluids in the tract of the urethral sleeve 100, consistent with an illustrative embodiment. As illustrated in FIG. 3B, the reservoir 110 is external from the distal end of the urethral sleeve 100. In one embodiment, there is a tab 306 at the distal end of the urethral sleeve 100 that is configured to open the seal 108 of the air lumen 106, thereby deflating the balloon 104. In this regard, FIG. 4 illustrates a urethral sleeve 100 having a deflated balloon, consistent with an illustrative embodiment. In one embodiment, the tab 306 is operative to also remove the urethral sleeve from the urethra. Stated differently, the pulling force applied to the tab 306 is operative to not only deflate the balloon 104 but also remove the urethral sleeve 100 from the urethra. In yet another embodiment, a tab is not required; rather by virtue of pulling the reservoir 110 with sufficient force allows to open the seal of the air lumen 106 and deflate the balloon. In this way, the entire urethral sleeve can be efficiently and quickly removed from the urethra.

Figure 5:
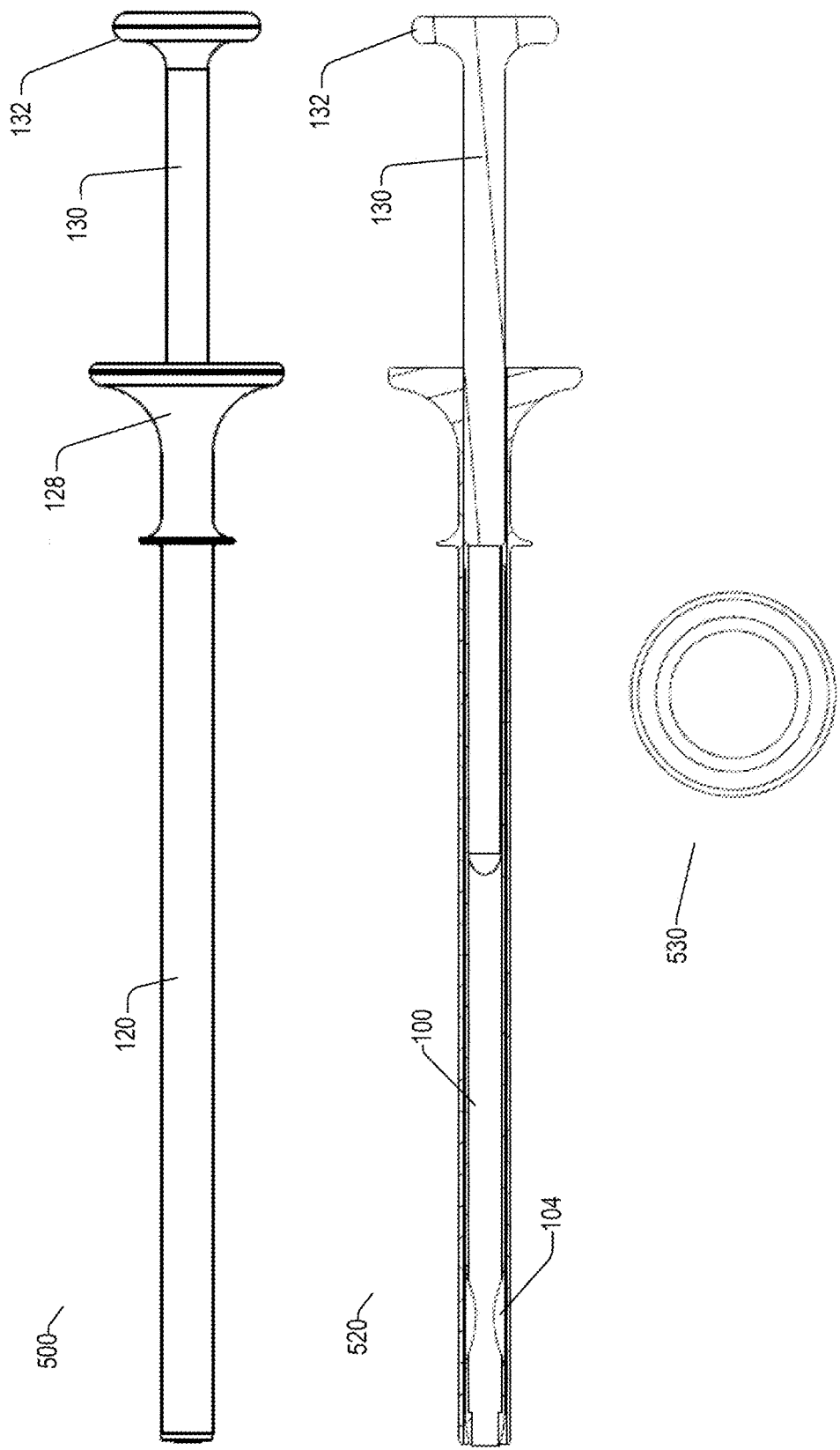
FIG. 5 provides a top, a cross-section, and a side view, respectively, of an example male intraurethral contraceptive system discussed in the context of FIGS. 1 to 4, drawn at a scale of 3, consistent with an illustrative embodiment.
Figure 6:
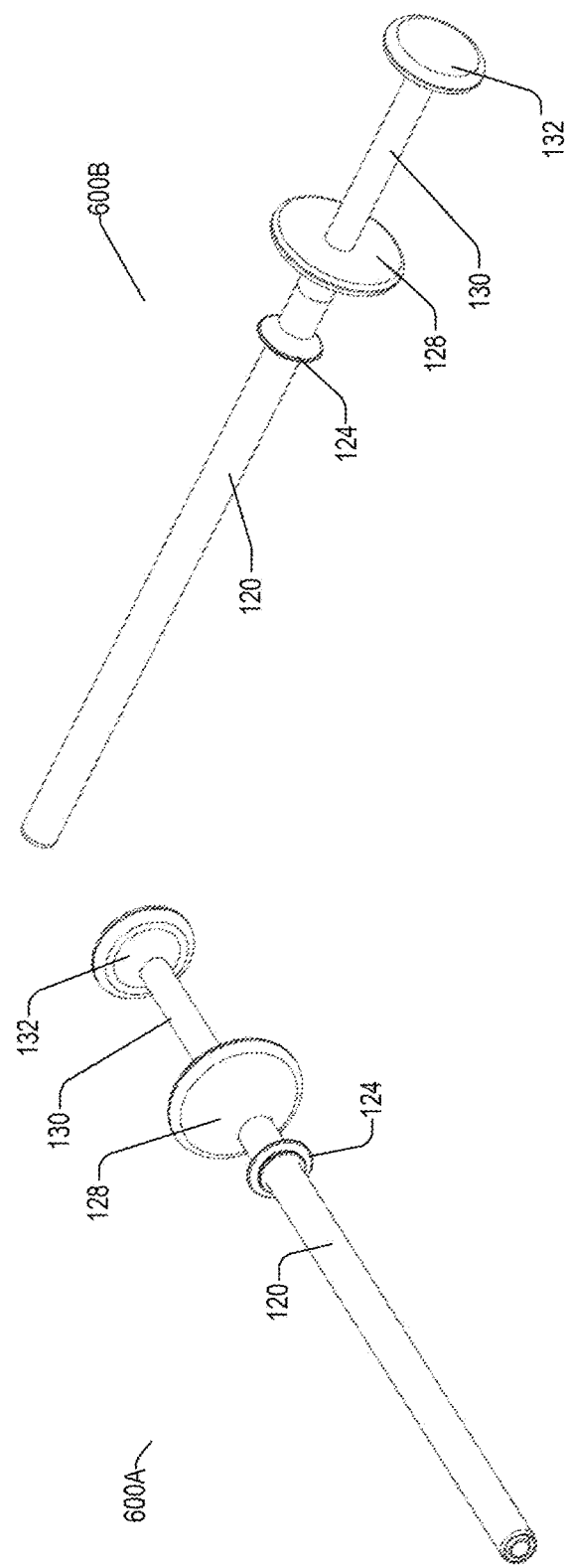
FIG. 6 provides perspective views from a proximal end and a distal end, respectively, of the intraurethral contraceptive system of FIG. 5, consistent with an illustrative embodiment.
Figure 7:
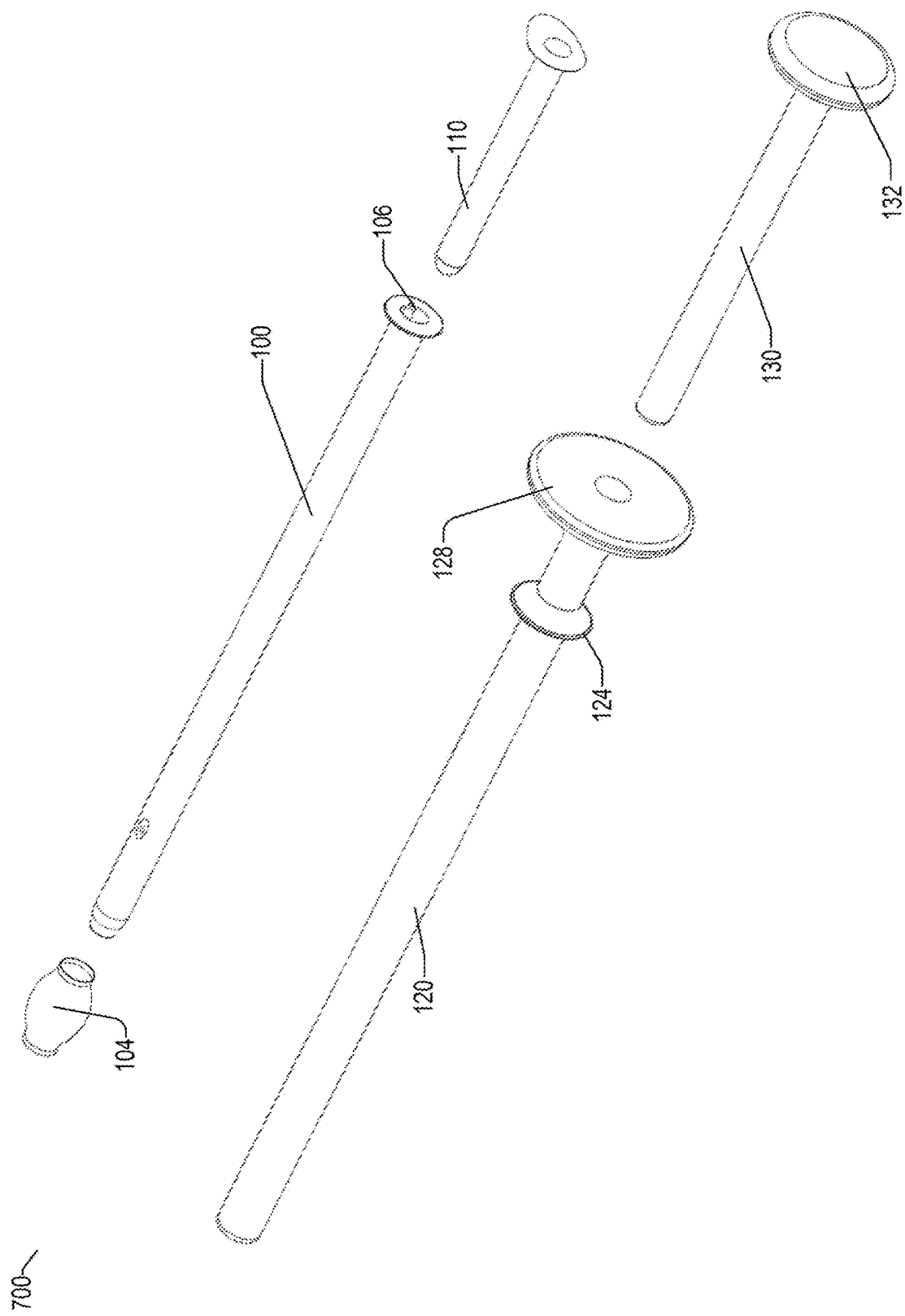
FIG. 7 provides an exploded view of the intraurethral contraceptive system of FIG. 5, consistent with an illustrative embodiment.

For a more detailed understanding of the concepts discussed herein, FIG. 5 provides a top 500, a cross-section 520, and a side view 530 of an example male intraurethral contraceptive system (ICS) discussed in the context of FIGS. 1 to 4 drawn at a scale of 3, consistent with an illustrative embodiment. FIG. 6 provides perspective views from a proximal end 600A and a distal end 600B of the ICS of FIG. 5, consistent with an illustrative embodiment. FIG. 7 provides an exploded view of an example intraurethral contraceptive system, consistent with an illustrative embodiment. It will be understood that the FIGS. 5 to 7 are provided as a conceptual overview of an ICS, and that many modifications and variations will be apparent to those of ordinary skill in the art without departing from the scope and spirit of the described embodiments. In one aspect, the intraurethral contraceptive devices discussed herein can be used with an external and/or internal lubricant that is bactericidal, virucidal, and/or spermicidal. The lubricant can also be associated with a vasodilator to help maintain an erection.

Example Process

Figure 8:
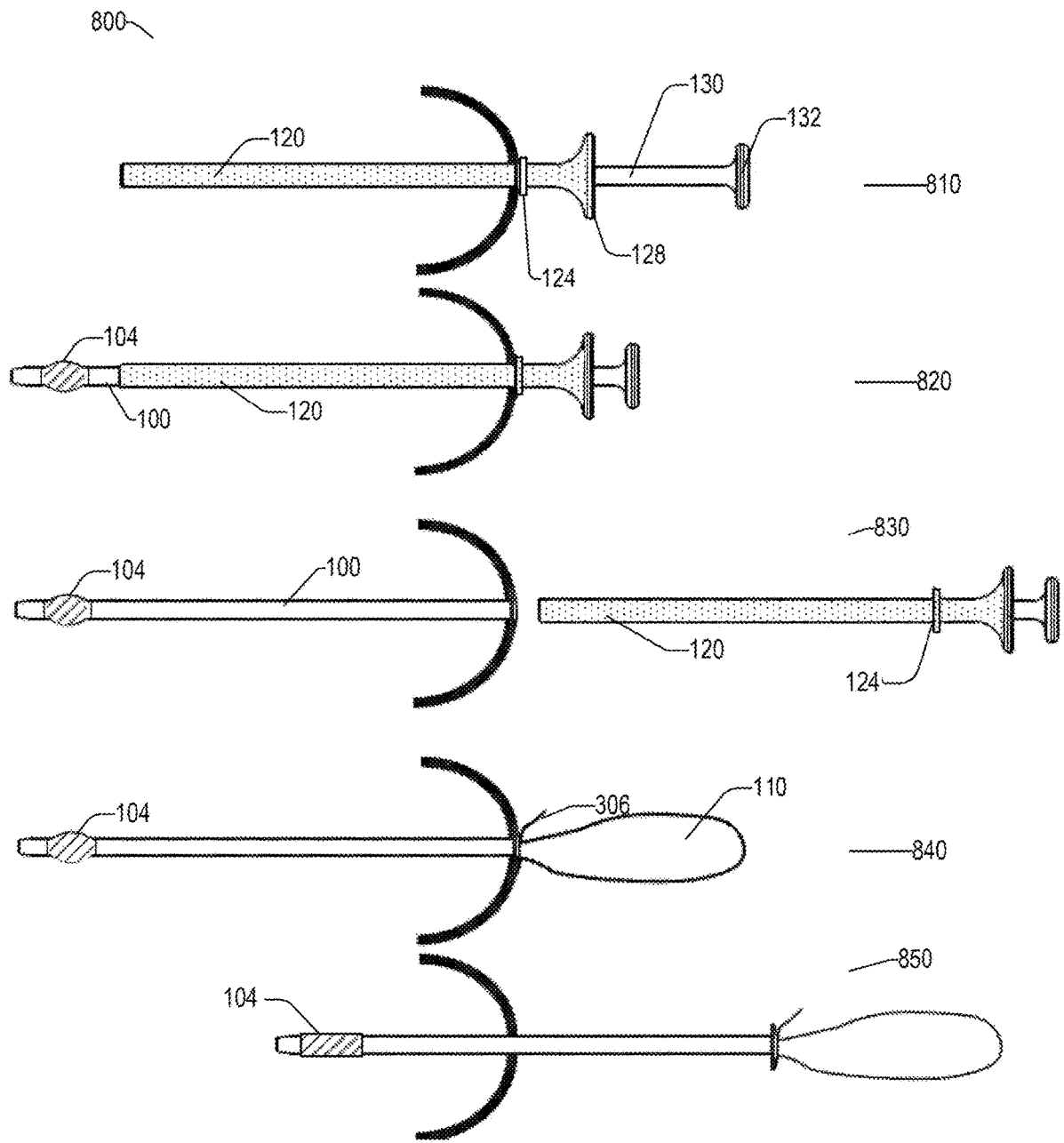
FIG. 8 presents a conceptual process of administering an intraurethral contraceptive device, consistent with an illustrative embodiment.

With the foregoing overview of the architecture of an ICS, it may be helpful now to consider a high-level discussion of an example process related thereto. To that end, FIG. 8 presents a conceptual process 800 of administering an intraurethral contraceptive device, consistent with an illustrative embodiment. For discussion purposes, the process 800 is described in a series of drawings 810 to 850 using components described in the context of the discussion of FIGS. 1 to 6.

In drawing 810, an intraurethral contraceptive device is shown having an insertion tool 120, a urethral sleeve inside the insertion tool 100, and an insertion plunger 130 at a distal end of the insertion tool. The insertion tool 120 is slidingly inserted into a urethra. In one embodiment, the insertion of the intraurethral device 100 into the urethra is stopped by an insertion stop 124 of the insertion tool 120.

In drawing 820, a proximal portion of the urethral sleeve 100 including a balloon 104 is released from a proximal end of the insertion tool 120 into the urethra. In one embodiment, the balloon is pre-inflated and expands upon release in the urethra, thereby anchoring the urethral sleeve 100 in the urethra. In various embodiments, the releasing of the proximal portion of the urethral sleeve 100 is by bringing a plunger head 132 of the insertion plunger 130 towards the plunger stop 128 of the insertion tool 120, by a predetermined distance, by either bringing the plunger head 132 to the plunger stop 128 and/or the plunger stop 128 towards the plunger head 132.

In drawing 830, the insertion tool 120 is slidingly removed from the urethra, together with the insertion plunger 132.

In drawing 840, any fluid traveling from the proximal end to the distal end of the urethral sleeve 100 is caught by a reservoir 110 coupled to a distal end of the urethral sleeve. In one embodiment, the reservoir 110 is initially within (i.e., inside) the urethral sleeve 100 and turns inside-out, thereby creating an external reservoir 110.

In drawing 850, the balloon is deflated. In one embodiment, the deflation of the balloon is by way of pulling a tab 306 at a distal end of the urethral sleeve, operative to open a seal of an air lumen leading to the balloon 104. In another embodiment, a separate tab is not necessary; rather, the deflation of the balloon 104 is facilitated by pulling the reservoir 110, which is operative to, in addition to catching fluids, to open a seal of an air lumen leading to the balloon 104 when pulled with sufficient force.

CONCLUSION

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

What is claimed is:

1. An intraurethral contraceptive device, comprising:
   an insertion tool configured to be inserted beyond a fossa navicularis of a penis;
   a urethral sleeve inside the insertion tool, the urethral sleeve comprising:
   a balloon on an outer surface at a proximal end of the urethral sleeve, having an air lumen that extends to a distal end of the urethral sleeve; and
   an inside reservoir at a distal end of the sleeve, configured to capture any fluid traveling from the proximal end to the distal end of the urethral sleeve; and
   an insertion plunger coupled to a plunger head, wherein the insertion plunger is configured to be placed inside a distal end of the insertion tool.

2. The device of claim 1, wherein the air lumen is sealed at the distal end of the urethral sleeve.

3. The device of claim 2, wherein the seal of the air lumen is by way of adhesion to an outer wall of the urethral sleeve.

4. The device of claim 1, wherein the air lumen is configured to inflate the balloon to a predetermined pressure and to deflate the balloon upon a trigger.

5. The device of claim 4, wherein the trigger to deflate the balloon through the air lumen is by way of a pullable tab at a distal end of the urethral sleeve.

6. The device of claim 1, wherein the insertion tool is constructed of a plastic material and is substantially cylindrically shaped.

7. The device of claim 1, wherein the insertion tool comprises a circumferential protruding member on an outer surface of the insertion tool configured to stop an insertion of the insertion tool into a urethra beyond a predetermined distance.

8. The device of claim 1, wherein:
   the insertion tool is configured to compress the balloon; and
   the balloon is pre-inflated.

9. The device of claim 1, wherein:
   the proximal end of the urethral sleeve is more rigid than its distal end; and
   a rigidity of the proximal end is sufficient to prevent the balloon from narrowing a diameter of an opening of the urethral sleeve below a predetermined threshold.

10. The device of claim 1, wherein the balloon is pre-inflated in the insertion tool.

11. The device of claim 1, wherein a distal end of the urethral sleeve is configured to not pass internally beyond the fossa navicularis of a penis.

12. The device of claim 1, wherein the proximal end of the insertion plunger abuts the distal end of the urethral sleeve inside the insertion tool.

13. The device of claim 1, wherein the insertion plunger is configured to slidingly release a proximal portion of the urethral sleeve including the balloon from a proximal end of the insertion tool into the urethra by a predetermined distance.

14. The device of claim 1, further comprising a vasodilator inside the insertion tool.

15. The device claim of claim 1, further comprising a stop at the distal end of the urethral sleeve that is configured to stop at the head of a glans penis and/or within a fossa navicularis within the glans penis, such that the stop is completely internalized and not visible externally.

16. A method of administering an intraurethral contraceptive device having an insertion tool, a urethral sleeve inside the insertion tool, and an insertion plunger at a distal end of the insertion tool, the method comprising:
slidingly inserting the insertion tool into a urethra beyond a fossa navicularis of a penis;
releasing a proximal portion of the urethral sleeve including a balloon from a proximal end of the insertion tool into the urethra;
slidingly removing the insertion tool together with the insertion plunger from the urethra;
leaving the urethral sleeve internalized within the fossa navicularis catching any fluid traveling from the proximal end to the distal end of the urethral sleeve by a reservoir coupled to a distal end of the urethral sleeve;
deflating the balloon; and
removing the urethral sleeve from the urethra.

17. The method of claim 16, further comprising controlling a predetermined distance that the insertion tool can be inserted into the urethra by a circumferential protruding member on an outer surface of the insertion tool.

18. The method of claim 16, wherein the balloon expands upon releasing the proximal portion of the urethral sleeve into the urethra.

19. The method of claim 16, wherein releasing of the proximal portion of the urethral sleeve comprises slidingly reducing a distance between a plunger head of the insertion plunger and the distal end of the insertion tool, by a predetermined distance.

20. The method of claim 16, wherein deflating the balloon comprises pulling a tab at a distal end of the urethral sleeve, operative to open a seal of an air lumen leading to the balloon.

21. The method of claim 16, wherein a stop at the distal end of the urethral sleeve is configured and positioned to stop at a head of a glans penis and/or within a fossa navicularis within the glans penis, such that the stop is completely internalized and not visible externally.

\* \* \* \* \*